United States Patent [19]
Yoshida

[11] Patent Number: 5,644,398
[45] Date of Patent: Jul. 1, 1997

[54] HOLE BURNING EFFECT MEASUREMENT SYSTEM

[75] Inventor: Haruo Yoshida, Gyoda, Japan

[73] Assignee: Advantest Corporation, Tokyo, Japan

[21] Appl. No.: 649,816

[22] Filed: May 17, 1996

[30] Foreign Application Priority Data

May 17, 1995 [JP] Japan .................................. 7-142512

[51] Int. Cl.$^6$ ................................................. G01B 9/02
[52] U.S. Cl. ......................... 356/349; 356/345; 356/351
[58] Field of Search ................................... 356/345, 351, 356/349, 359, 360, 346

[56] References Cited

U.S. PATENT DOCUMENTS

| | | | |
|---|---|---|---|
| 5,469,259 | 11/1995 | Golby et al. | 356/351 |
| 5,486,919 | 1/1996 | Tsuji et al. | 356/349 |
| 5,523,839 | 6/1996 | Robinson et al. | 356/351 |

*Primary Examiner*—Frank Gonzalez
*Assistant Examiner*—Robert Kim
*Attorney, Agent, or Firm*—Knobbe, Martens, Olson & Bear, LLP

[57] ABSTRACT

A hole burning measurement system realizes accurate analysis of a photochemical hole burning effect in an optical device. The hole burning measurement system includes, a light source for generating a coherent light beam, a first beam splitter for splitting the coherent light beam into two light beams; an optical frequency shifter for shifting a frequency of one of the two light beams splitted to form a reference light beam, an optical switch for switching the other light beam splitted by the first beam splitter to form a pulse train in a form predetermined for inducing photon echoes in the optical device under test; a circular polarization converter for circularly polarizing the pulse train to form a circularly polarized light pulse train; a second beam splitter for mixing the reference light beam and a free induction decay (FID) signal of the photon echo induced by the pulse train in the optical device under test; a photo detector for converting a mixed signal from the second beam splitter to a corresponding electric signal; an analog-to-digital converter for converting the electric signal to corresponding digital data; and a Fourier transformer for converting the digital data from the analog-to-digital converter to frequency domain data showing the hole burning effect in a form of frequency spectrum.

15 Claims, 6 Drawing Sheets

PHB HOLES

HOLE BURNING EFFECT MEASUREMENT SYSTEM

FIELD OF THE INVENTION

This invention relates to a measurement system which analyzes a photochemical hole burning effect in optical devices or materials, and more particularly, to a hole burning effect measurement system to measure photon echoes generated by optical devices such as an optical amplifier or an optical fiber in response to excitation by a light pulse train to accurately analyze a photochemical hole burning phenomenon in such optical devices.

BACKGROUND OF THE INVENTION

A photochemical hole burning (PHB) effect is a phenomenon arises in an optical device when, for example, a monochromatic light is emitted to dye molecules monodispersed in a material such as polymer film or organic glass. In such a hole burning effect, a hole of a reduced absorption coefficient is created in the wavelengths of absorption spectra of the molecules. Once created, such a hole almost permanently stays in the exists in the optical device.

In other words, when the guest molecules such as the dispersed dye molecules or ions exist in the host molecules such as the organic glass or polymer film, a uniform and narrow range of lower absorption coefficient hole appears in the ununiformly dispersed optical absorption spectra of the guest molecules.

The PHB is induced by a chemical change of material in a broad sense, such as optical isomerism, ionization of guests such as dye molecules or positional change of the guests in the host molecules, caused by optical excitation. The reduction of the absorption coefficient is also arises when there is a structural change in the hosts surrounding the guests. This is called a photophysical hole burning. In this invention the PHB includes this photophysical hole burning effect.

The PHB effect has attracted attention as a principle of operation in an optical memory. Since the PHB causes a birefringence of optical beam, in a telecommunication filed, it has also attracted attention as a cause of optical polarization.

As of today, there is no specific measuring instrument to measure the PHB effects. One possible method is a saturation spectroscopy in which a high power laser is used as a pump light while a variable frequency laser such as a dye laser is used as a frequency sweeper.

The recent development of a long distance, large volume optical communication technology owes to low loss optical fibers and high gain, wide frequency range and low noise optical amplifiers. However, with the development of performance in such optical components, it has been realized that the polarization dependency in the materials of such optical components is now a significant factor that limits the further development of performance.

This polarization dependency, which deteriorates a signal to noise (S/N) ratio, is caused by a polarization dispersion, a polarization dependent loss or a polarization hole burning. Art example of the polarization hole burning in this case is a phenomenon arises when a signal light incidents to an optical fiber amplifier doped with erbium in which gains are slightly different between a direction of the signal light and a direction perpendicular to the signal light.

Under this phenomenon, since noises in a spontaneous emitted light which are perpendicular to the signal light are amplified with higher gain, the overall S/N ratio decreases. Similar problems also arise in the optical fiber. At present, there is not an appropriate measuring method to accurately analyze these problems.

Further, there is not an effective method for measuring a PHB effect to be used in a multi-wavelength ultra high density optical memory. In the measuring method of saturation spectroscopy as mentioned above, the PHB effect may change because the temperature of the host materials increases when a higher power laser light is applied to the host materials. If a lower power laser light is used, since a half width of a multiple resonance is small, a slow frequency sweep is necessary to avoid any transitional responses, which requires a longer measurement time. Further, in an optical communication field, not only to measure the PHB phenomenon in the optical devices but is also necessary to quantitatively analyze the polarization dependency induced by the PHB.

SUMMARY OF THE INVENTION

Therefore, it is an object of the present invention to provide a hole burning effect measurement system to measure photochemical hole burning effects related to both a optical communication field and a optical memory field by the same technical concept.

It is another object of the present invention to provide a hole burning effect measurement system which is capable of analyzing a photochemical hole burning effect in an optical memory as well as a polarization photochemical hole burning effect in optical communication devices such as an optical amplifier or an optical fiber.

It is a further object of the present invention to provide a hole burning effect measurement system which is capable of accurately analyzing a photochemical hole burning effect with the use of a low power light pulse so that the hole burning effect is not affected by the temperature of the host materials.

It is a further object of the present invention to provide a hole burning effect measurement system which is capable of analyzing a photochemical hole burning effect with high sensitivity by utilizing an averaging technology in processing photon echoes from the optical device under test induced by the measurement system.

It is a further object of the present invention to provide a hole burning effect measurement system which is capable of analyzing a photochemical hole burning effect with high sensitivity by utilizing a heterodyne technology whereby optical signal frequencies are converted to a lower frequency electric signal.

In the present invention, a resonant optical pulse train from a coherent light source is applied to a optical device under test (DUT) and the resulted photon echo generated by the DUT is detected and analyzed by the hole burning measurement system.

The hole burning measurement system of the present invention includes: a light source for generating a coherent light beam; a first beam splitter for splitting the coherent light beam into two light beams; an optical frequency shifter for shifting a frequency of one of the two light beams splitted by the first beam splitter to form a reference light beam; an optical switch for switching the other light beam splitted by the first beam splitter to form a pulse train in a form predetermined for inducing photon echoes in the optical device under test; a circular polarization converter for circularly polarizing the pulse train from the optical switch to form a circularly polarized light pulse train to be applied to the optical device under test; a second beam splitter for mixing the reference light beam and a free induction decay (FID) signal of the photon echo induced by the pulse train in the optical device under test; a photo detector for receiving a mixed signal from the second beam splitter and converting the same to a corresponding electric signal; an analog-to-digital converter for converting the electric signal to corresponding digital data; and a Fourier transformer for converting the digital data from the analog-to-digital converter to frequency domain data showing the hole burning effect in a form of frequency spectrum.

In another aspect of the present invention, a birefringence prism is provided after the second beam splitter to separate polarization components which are perpendicular with each other in the photon echo FID signal. Thus, the hole burning measurement system includes a pair of photo detectors and a pair of analog-to-digital converters. Each of the polarization component is converted to an electric signal by the corresponding photo detector and further converted to digital data by the corresponding analog-to-digital converter. By providing a Fourier transformation process for both of the digital data, the polarization hole burning effect in the optical device can be analyzed.

According to the present invention, the hole burning effect measurement system can measure photochemical hole burning effects related to both an optical communication field and an optical memory field by the same technical concept, i.e. photon echoes excited by light pulses and a frequency heterodyne technology. The hole burning effect measurement system of the present invention is capable of analyzing the photochemical hole burning effects in the optical memory as well as in the optical communication devices such as an optical amplifier or an optical fiber.

The hole burning effect measurement system of the present invention accurately analyzes the photochemical hole burning effect with the use of low power light pulses so that the hole burning effect is not affected by the temperature of the host materials. Further, the hole burning effect measurement system analyzes the photochemical hole burning effect with high sensitivity by utilizing an averaging technique in processing photon echoes from the optical device under test induced by the measurement system.

DETAILED DESCRIPTION OF THE PREFERRED EMBODIMENT

FIGS. 1 and 2 respectively show first and second embodiments of the hole burning measurement system of the present invention. In the present invention, a resonant optical pulse train from a coherent light source is applied to an optical device under test (DUT) and the resulted photon echo generated by the DUT is detected and analyzed by the hole burning measurement system.

Before going into details of the embodiments of the present invention, a brief description regarding the photon echo used in the present invention is given in the following. More detailed explanation is given, for example, in "Encyclopedia of Lasers and Optical Technology" page 373–375, 1991, Academic Press.

Figure 3A:
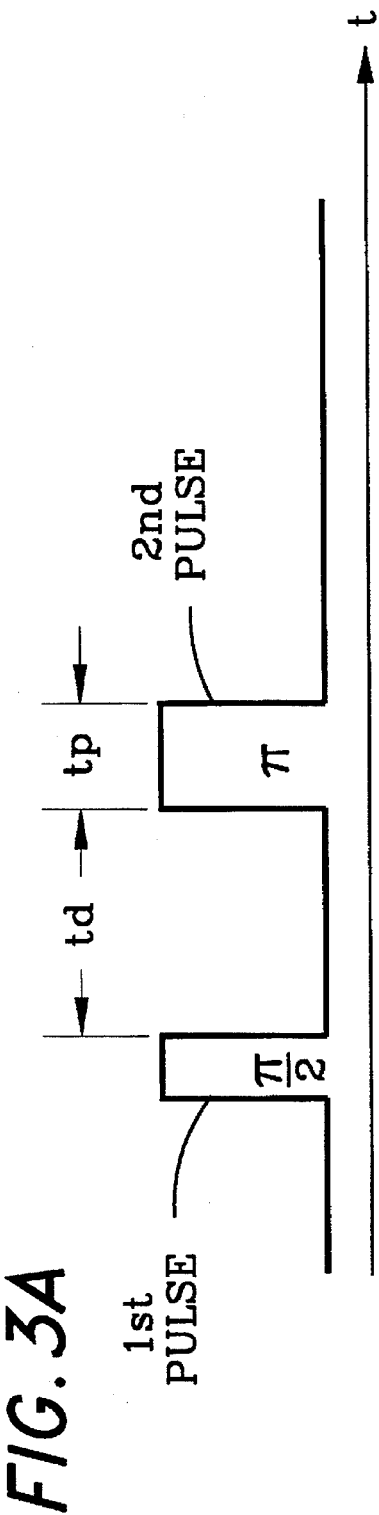
FIG. 3A is a waveform diagram showing a resonant optical pulse train to be emitted to the optical device under test to explain a photon echo induced in the optical device.
Figure 3B:
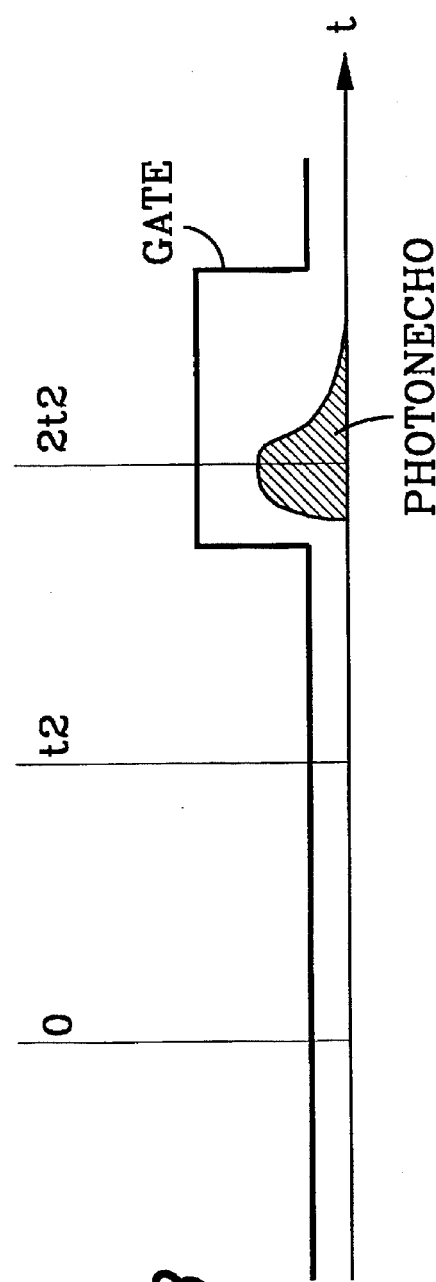
FIG. 3B is a waveform diagram showing a free induction decay (FID) of the photon echo induced by the resonant optical pulse train of FIG. 3A.

A photon echo is a phenomenon in which a coherent pulse of light (called an "echo") is generated in a nonlinear medium at a characteristic time after two other pulses, separated by a certain time interval, have entered to the medium. FIG. 3 shows a simplest model for explaining the photon echo which is caused by two resonant laser pulses to excite the medium (optical device) such as an optical amplifier or an optical fiber. FIG. 3A shows the resonant optical pulses applied to the optical device and FIG. 3B shows a free induction decay (FID) of the photon echo from the optical device.

A first optical pulse having an area $\pi/2$ is irradiated to the optical device (DUT), for example an optical amplifier or an optical fiber, the excitations of the DUT are dephased and canceled one another almost immediately. After a time $t_a$, if a second optical pulse having an area $\pi$, a time width $t_p$, and a center time $t_2$ is irradiated to the DUT, the transition of dephasing as noted above is inversed with respect to time. As a result, after the time $t_2$, the situation before the dephasing is reproduced and photon echoes are emitted from the DUT as shown in FIG. 3B.

The amplitude of the photon echoes is a function of the time $t_2$ and is exponentially reduced. This reduction of the amplitude is called a free induction decay (FID). It is known that the reduction curve of the FID and the shape of the photochemical hole burning (PHB) are in the Fourier transform relationship. Thus, by detecting the photon echoes from the DUT and providing a Fourier transform process to the detected data, the characteristics of the PHB of the DUT will be analyzed.

Figure 4A:
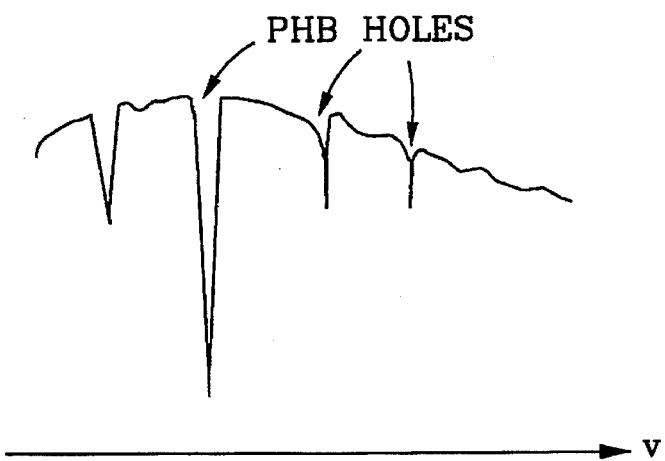
FIG. 4A is a schematic diagram showing an example of hole burning spectra.
Figure 4B:
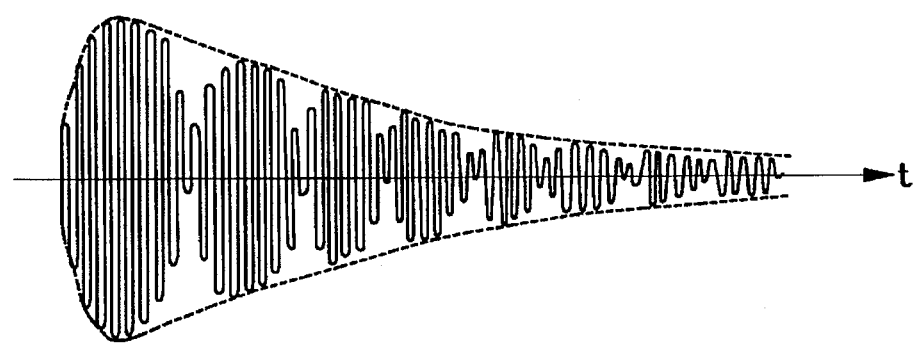
FIG. 4B is a schematic diagram showing an example of free induction decay (FID) of the photon echo representing holes produced by the photochemical hole burning effect in the optical device under test.
Figure 4C:
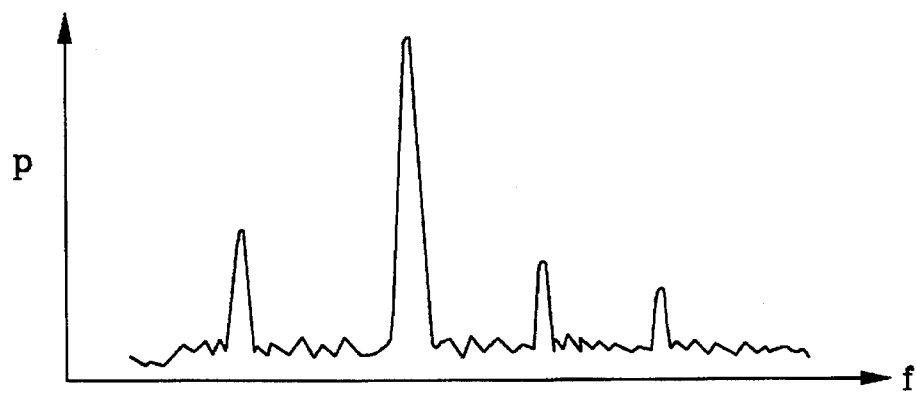
FIG. 4C is a schematic diagram showing an example of spectra obtained by a Fourier transform of the photon echo of FIG. 4B.

FIG. 4 shows the relationship between the photon echoes and the PHB and the frequency spectra of the PHB obtained from the photon echo. FIG. 4A shows an example of holes seen by the hole burning effect of the DUT and FIG. 4B shows an example of the free induction decay (FID) of the photon echoes representing the holes of FIG. 4A, and FIG. 4C shows an example of frequency domain spectra obtained through the Fourier transform of the photon echoes of FIG. 4B. As in FIG. 4C, the hole burning parameters of the DUT is measured in the frequency domain, i.e., the sizes of the holes are expressed by the amplitudes of the spectra and the wavelengths of the holes are expressed by the frequency dispersions.

In the example of FIG. 3, the two resonant optical pulses are used to excited the optical device under test. Other methods are also available to produce the photon echoes in the optical device such as an induction echo including three or more resonant laser pulses to be emitted to the device under test.

Referring back to FIGS. 1 and 2, the embodiments of the present invention will be described in detail below. In the hole burning measurement system of the present invention, the photon echo noted above is applied to an optical system based on a heterodyne principle. Under the heterodyne principle, a signal to be measured and a reference signal having different frequencies are mixed together and the frequency of the signal to be measured is converted to the difference of the two signals.

Figure 1A:
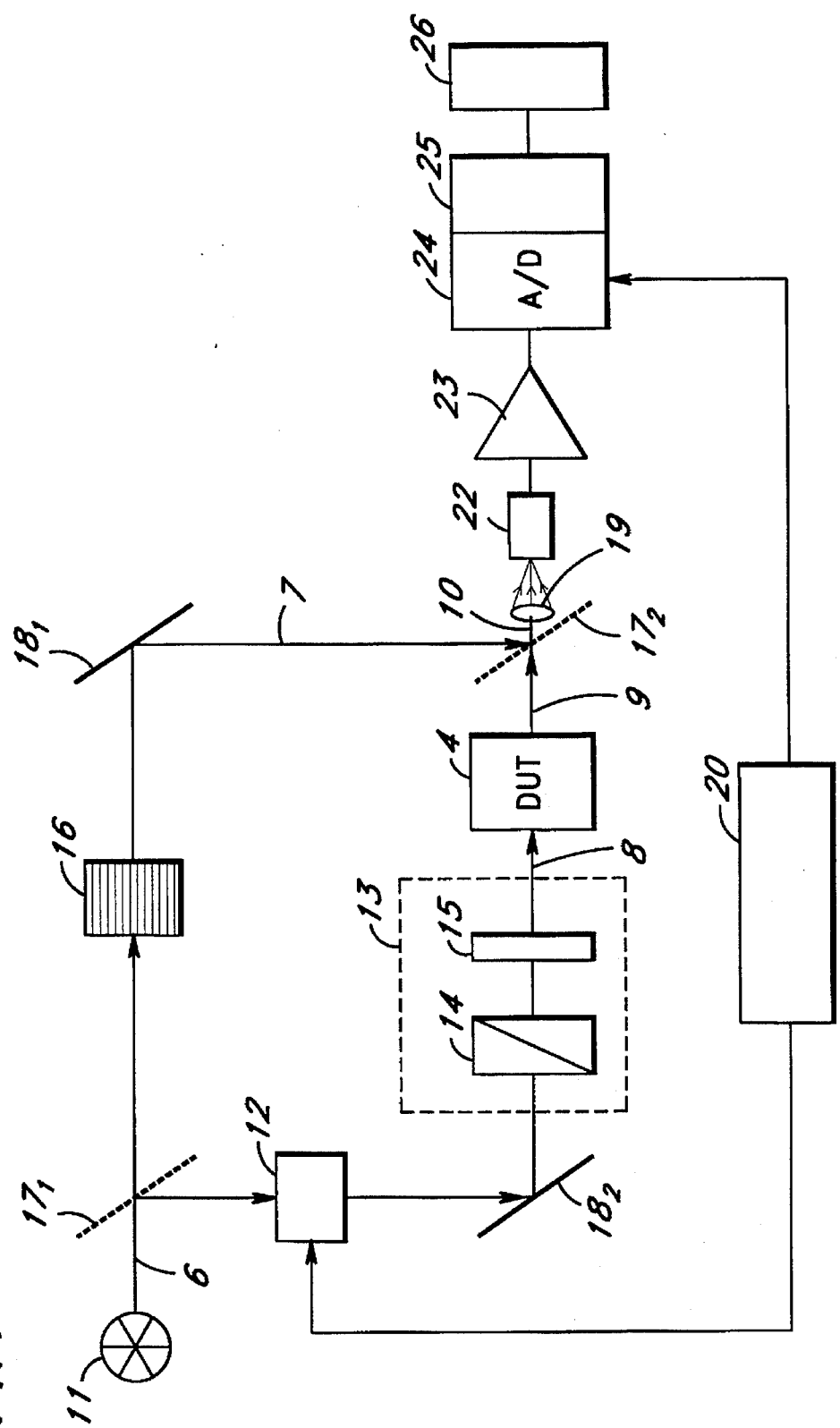
FIG. 1A is a schematic diagram showing a structure of a first embodiment of a hole burning measurement system for measuring a transmission type optical device according to the present invention.
Figure 2A:
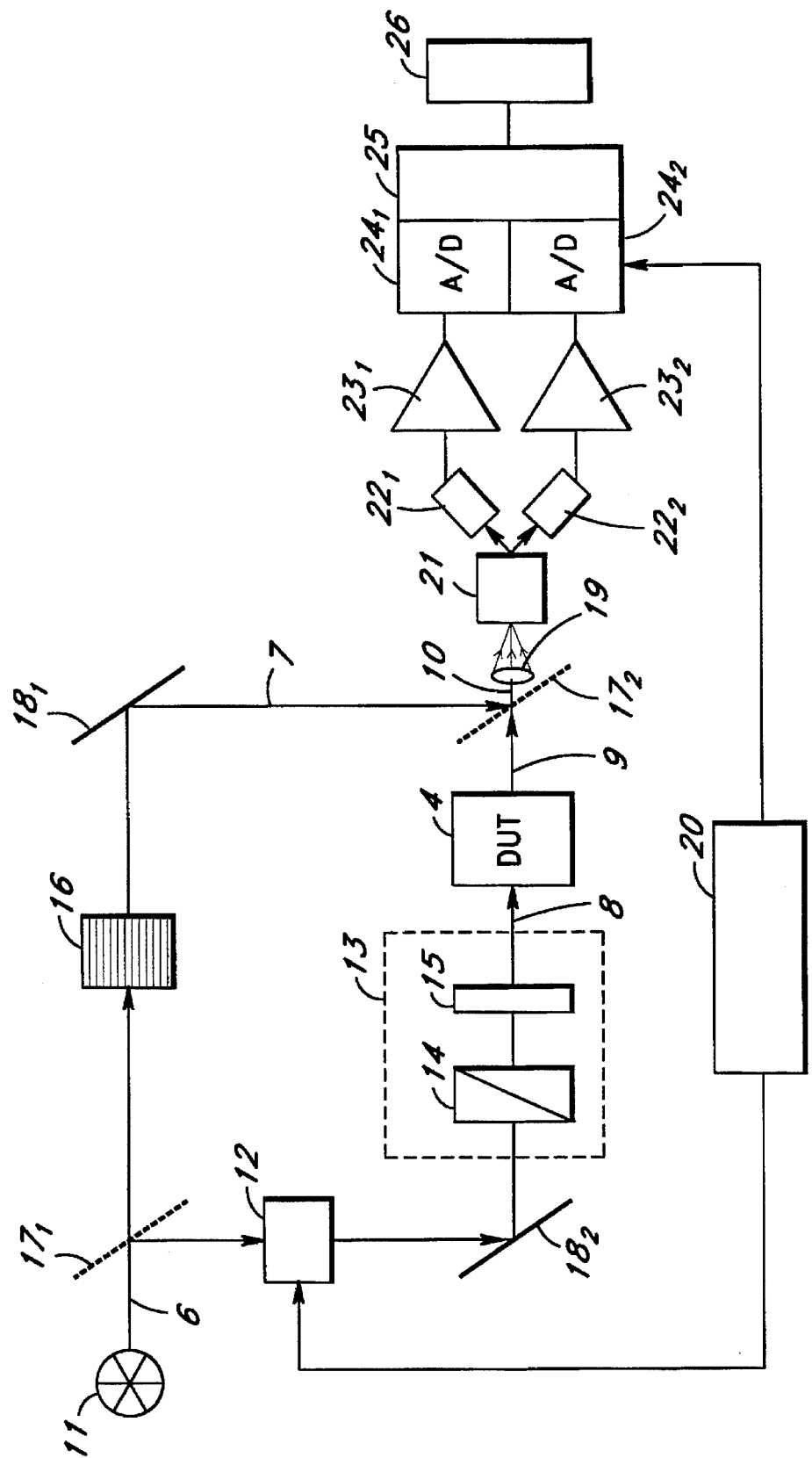
FIG. 2A is a schematic diagram showing a structure of a second embodiment of a hole burning measurement system for measuring a transmission type optical device according to the present invention.
Figure 1B:
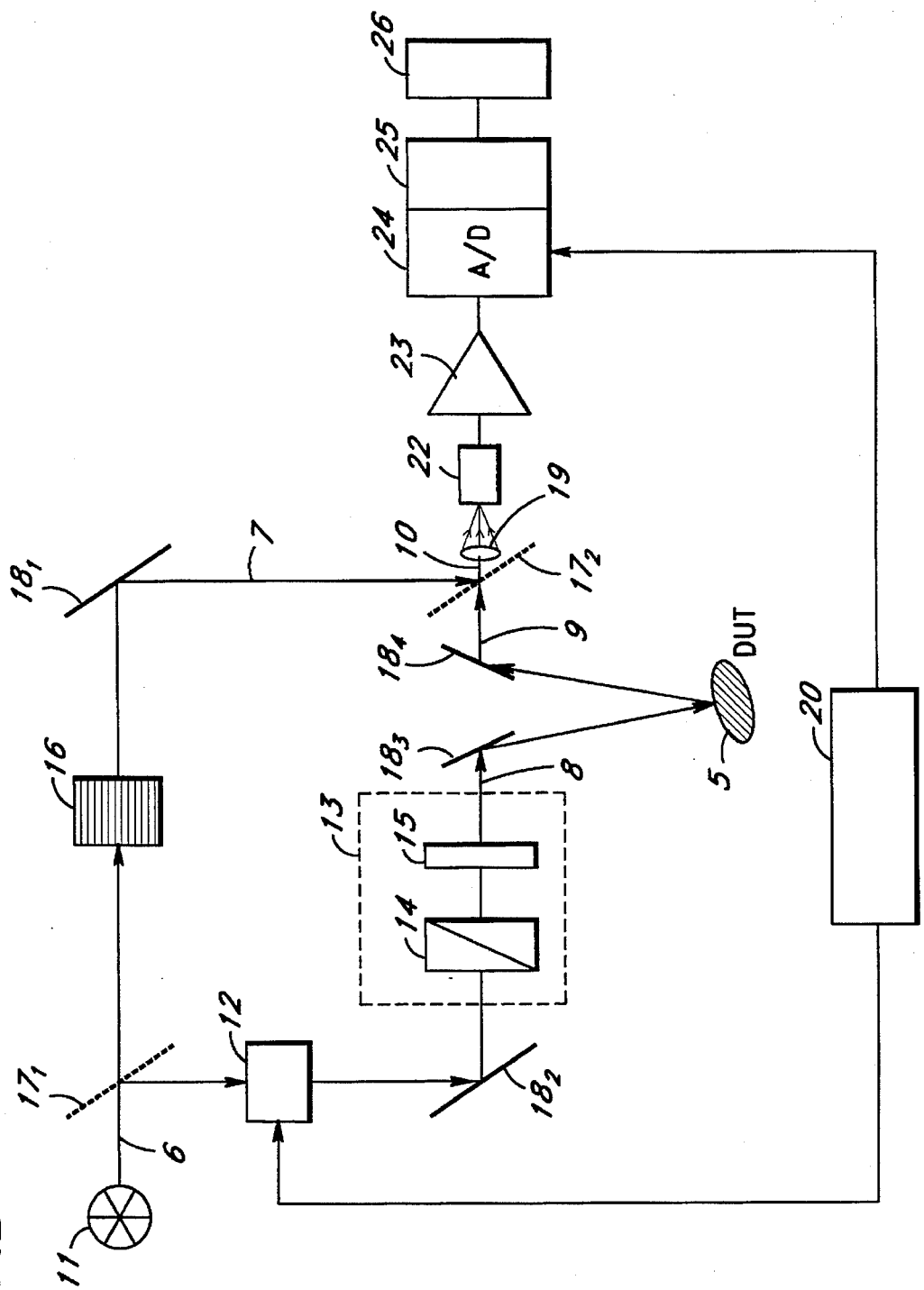
FIG. 1B is a schematic diagram showing a structure of the first embodiment of a hole burning measurement system for measuring a reflection type optical device according to the present invention.
Figure 2B:
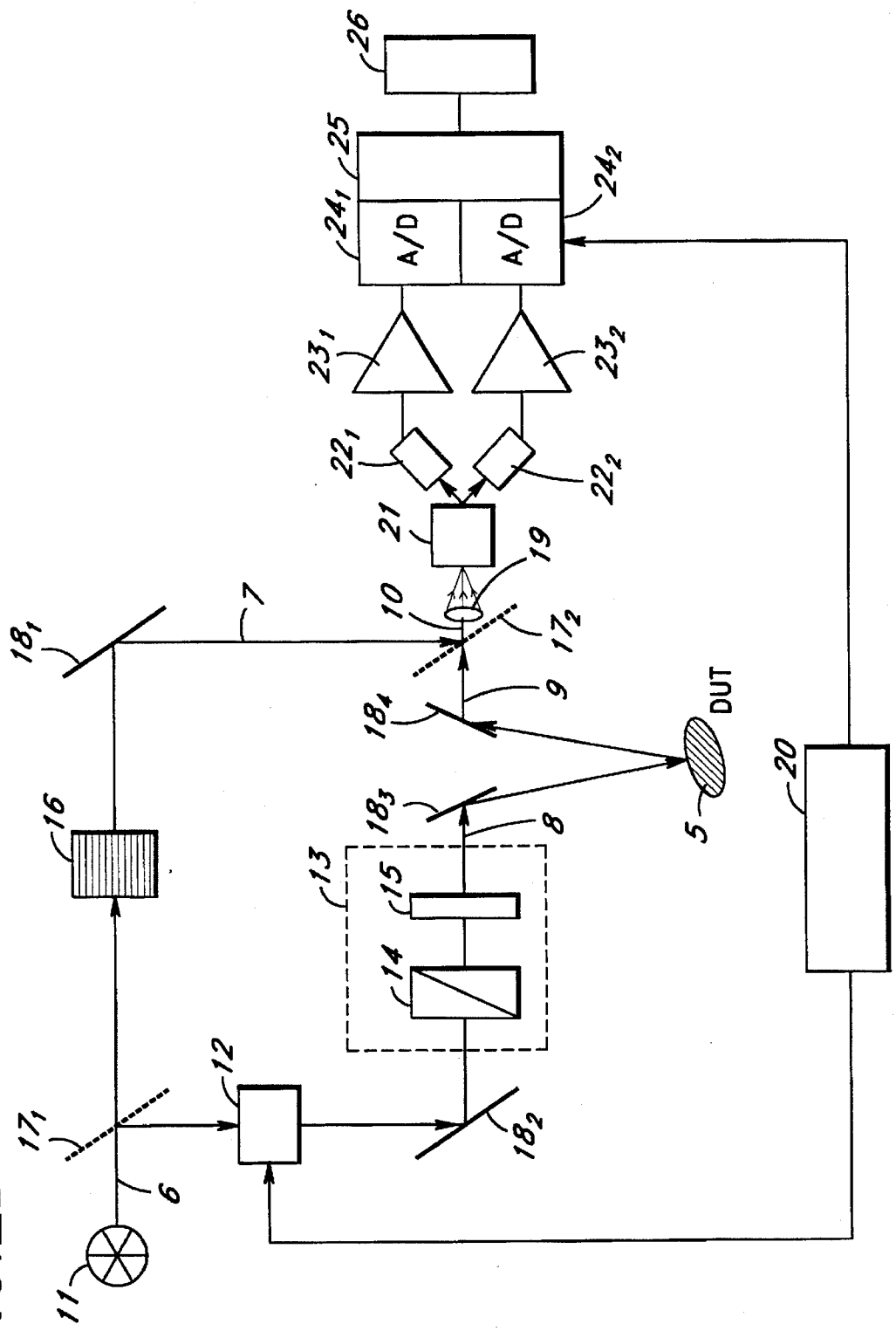
FIG. 2B is a schematic diagram showing a structure of the second embodiment of a hole burning measurement system for measuring a reflection type optical device according to the present invention.

The embodiment of FIGS. 1A and 1B is a hole burning measurement system to analyze a photochemical hole burning in an optical device such as an optical fiber, an optical amplifier and an optical memory with the use of a lower power input light. The embodiment of FIGS. 2A and 2B is a hole burning measurement system to analyzed a polarization dependency of optical devices and materials caused by a photochemical hole burning effect.

In the example of FIG. 1A, the hole burning measurement system of the present invention includes a light source 11, beam splitters $17_1$ and $17_2$, an optical switch 12, an optical frequency shifter 16, reflectors such as mirrors $18_1$ and $18_2$, a circular polarization converter 13 which is formed for example of a polarizer 14 and a λ/4 plate 15, a timing pulse generator 20, a lens 19, a photo detector 22, an amplifier 23, an A/D converter 24, an arithmetic unit such as a calculator 25 and a display 38. An optical device under test (DUT) 4 is inserted between the circular polarization converter 13 and the beam splitter $17_2$. The DUT in this example is a transmission type optical device such as an optical fiber or an optical amplifier.

The light source 11 generates a coherent light beam 6 which is for example a linearly polarized light. The light beam 5 is splitted into two light beams by the beam splitter $17_1$. One light beam splitted by the beam splitter $17_1$ is frequency shifted by the optical frequency shifter 16. The optical frequency shifter 16 includes, for example, an acousto-optic effect element to frequency shift the incoming light beam. Such frequency shift is preferably in a range from several Mhz to 100 MHz which is a frequency range easily handled by electric circuits including the amplifier 23 and the A/D converter 26.

The frequency shifted light beam 7 is used as a reference light beam and can be the linearly polarized light beam as emitted from the light source 11. However, it is preferable to convert the light beam 7 to a circularly polarized light for an improved measurement sensitivity and convenience of a signal processing in the later stage. Thus, although not shown, a circular polarization convener may be preferably included before or after the frequency shifter 16. The reference light beam 7 is provided to the beam splitter $17_2$ via the mirror $18_1$.

The other light beam splitted by the beam splitter $17_1$ is used as a probing light beam which is a pulse train 8 to be applied to the DUT 4. The pulse train 8 is provided to the DUT through the optical switch 12, the circular polarization converter 13 via the mirror $18_2$. To induce photon echoes in the DUT 4, the resonant pulse train having the specific relationship between the adjacent two pulses must be irradiated to the DUT 4 as noted above with respect to the principle of the photon echo in FIG. 3. Such a resonant optical pulse train is established by the optical switch 12 which switches the incoming light beam from the beam splitter $17_1$ based on a timing signal provided from the timing generator 20.

The resonant pulse train may take various forms such as a two pulse method, a three pulse method and the like. The relationship between the pulses in terms of the pulse width, pulse area and time interval are theoretically determinable to induce the photon echoes from the optical device under test. Thus, the timing generator 20 provides a timing signal which drives the optical switch to output the pulses having the predetermined pulse width, the pulse area and the time interval from the optical switch.

Many types of optical switch are known in the art and applicable to the present invention. An example of the optical switch suitable for this invention is a piezoelectric bimorph end-fire switch which employs a piezoelectric element to move an input fiber relative to an output fiber when a control voltage (timing signal) is applied. Other example is a liquid crystal switch in which a liquid crystal layer is sandwiched between glass prism to apply the control voltage (timing signal) to control the direction of molecules in the liquid crystal which changes the refractive index seen by a light passing through the layer. An optical switch using an acoustooptic effects is also applicable to the present invention in which a high frequency acoustic wave in a crystal is used to deflect an optical beam at an angle dependent on the frequency applied to an electroacoustic transducer. More detailed description is given, for example, in "Encyclopedia of Lasers and Optical Technology" page 633–643, 1991, Academic Press.

The pulsed light beam from the optical switch 12 is provided to the circular polarization converter 13 where it is circularly polarized. Thus, at the output of the circular polarization converter 13, a circularly polarized pulse train 8 is generated which is supplied to the DUT 4.

As noted above, by applying the laser pulse train 8 to the DUT 4, the photon echoes are induced in the DUT 4 whereby generates a free induction decay (FID) signal 9. The FID signal 9 is mixed with the reference light beam 7 by the beam splitter $17_2$ whereby the FID signal 9 is converted to a mixed signal 10 including a lower frequency signal. The lower frequency signal in the mixed signal 10 has a frequency equal to the frequency shift given to the reference beam 7 by the optical frequency shifter 16.

As noted above, although the reference light beam 6 can be a linearly polarized, a circularly polarized light beam is preferable for measuring the FID signal 9 with higher sensitivity. The lower frequency signal in the mixed signal 10 includes all of the information in the FID signal 9 regarding the hole burning effect in the DUT 4.

Prior to applying to the photo detector 22, the mixed signal 10 from the beam splitter $17_2$ is preferably focused by the lens 19. The photo detector 22 converts the incoming light signal to a corresponding electric signal. The electric signal detected by the photo detector 22 in this manner shows the low frequency which is a difference between the reference light beam 7 and the FID signal 9, i.e., the frequency shifted by the frequency shifter 16. The electric signal thus produced has all the information regarding the photon echo FID of the DUT 4.

If necessary, the electric signal may be further down converted its frequency or may be amplified by the amplifier 23. As noted above, the electric signal have frequencies of several Mhz to 100 MHz based on the frequency shift by the frequency shifter 16. Thus, it may be also possible to provide a band pass filter for such a frequency so that noises such as random noise will be reduced at the output of the band pass filter.

The A/D converter 24 converts the electric signal into corresponding digital data having the information of the photon echo FID. The digital data may preferably be stored in memories in the A/D converter 24. Preferably, the operation of the A/D converter 24 is synchronized with a gate signal (FIG. 3B) from the timing generator 20.

The calculator 25 performs a Fourier transformation for the digital data acquired by the A/D converter 24. The Fourier spectra resulted from this transformation is frequency domain information showing the frequency spectra representing the photochemical hole burning effect in the DUT 4. The Fourier spectra are displayed on the display 26 in a manner shown in FIG. 4C or stored in a memory or transferred to a network for further use.

FIG. 1B shows an arrangement of the present invention in which an optical device under test (DUT) 5 is a reflection type device where the light beam is reflected from the device under test rather than passing therethrough. An example of the reflection type optical device is an optical memory. In the example of FIG. 1B, only the manner of applying the pulsed light beam to the DUT 5 and receiving the resulting photon echo FID signal from the DUT 5 is different from the example of FIG. 1A. To do so, the hole burning measurement system additionally includes mirrors (reflectors) $18_3$ and $18_4$ to guide the light beams. The other parts of the invention are the same as in the invention of FIG. 1A.

The pulsed light beam 8 from the circular polarization converter 13 is changed its direction by the mirror $18_3$ and is irradiated on the DUT 5. The resulting photon echo FID signal 9 from the DUT 5 is guided by the mirror $18_4$ to be supplied to the beam splitter $17_2$ where it is mixed with the reference light beam 7. As noted above with reference to FIG. 1A, since the reference light beam 7 is frequency shifted by the frequency shifter 16, the mixed signal 10 is a light signal having the beat frequency of which is a difference between the reference light beam 7 and the photon echo FID signal 9. In the same manner as described with reference to FIG. 1A, the frequency converted signal in the mixed signal 10 is converted to the electric signal which is further transformed to the Fourier spectra.

FIG. 2 is a block diagram showing a structure of the second embodiment of the hole burning measurement system of the present invention for analyzing a polarization hole burning effect of an optical device. Like in the cases of FIG. 1, the configuration of FIG. 2A is for measuring a transmission type optical device such as an optical fiber or an optical amplifier while the configuration of FIG. 2B is for measuring a reflection type optical device such as an optical memory.

In the example of FIG. 2A, the hole burning measurement system of the present invention includes a light source 11, beam splitters $17_1$ and $17_2$, an optical switch 12, an optical frequency shifter 16, reflectors such as mirrors $18_1$ and $182$, a circular polarization converter 13 which is formed of a polarizer 14 and a λ/4 plate 15, a timing pulse generator 20, a lens 19, a birefringence prism 21, a pair of photo detectors $22_1$ and $22_2$, a pair of amplifiers $23_1$ and $23_2$, a pair of A/D converters $24_1$ and $24_2$, an arithmetic unit such as a calculator 25 and a display 38. An optical device under test (DUT) 4 is inserted between the circular polarization converter 13 and the beam splitter 172.

The example of FIG. 2B is structurally different from the example of FIG. 1A only after mixing the reference light beam 7 and the photon echo FID signal 9 by the beam splitter $17_2$. In the second embodiment, polarization components or polarized planes in the mixed signal 10 which are perpendicular with each other are separated. Each of the polarization components, P and S for example, is measured with respect to the photochemical hole burning to analyze the polarization effect of the hole burning in the optical device under test.

For doing this, the mixed signal 10 is focused by the lens 19 and is received by the birefringence prism 21 which is typically a Wollaston prism. Each of the polarization components separated by the birefringence prism 21 is converted to an electric signal by the corresponding photo detectors $22_1$ and $22_2$. The electric signals detected by the photo detectors $22_1$ and $22_2$ in this manner have a beat down frequency which is a difference between the reference light beam 7 and the photon echo FID signal 9, i.e., the frequency shifted by the optical frequency shifter 16.

The photon echo FID signal in each of the polarization components p and S is amplified, if necessary, and converted to digital data by the A/D converters $24_1$ and $24_2$. The digital data are stored in memories in the A/D converters. The calculator 25 carries out a Fourier transform for the digital data with respect to both of the polarization components. Thus, the resulted Fourier spectra indicate the frequency characteristics of the photon echo FID signal of each polarization. The Fourier spectra are displayed on the display 26 in a manner shown in FIG. 4C or stored in a memory or transferred to a network for further use.

FIG. 2B shows a modification of the second embodiment of the present invention in which an optical device under test (DUT) 5 is a reflection type device where the light beam is reflected from the device under test rather than passing therethrough. An example of the reflection type optical device is an optical memory. In the example of FIG. 2B, only the manner of applying the pulsed light beam to the DUT 5 and receiving the resulting photon echo FID signal from the DUT 5 is different from the example of FIG. 2A. To do so, the hole burning measurement system additionally includes mirrors (reflectors) $18_3$ and $18_4$ to guide the light beams. The other parts of the invention are the same as in the invention of FIG. 2A.

The pulsed light beam 8 from the circular polarization converter 13 is changed its direction by the mirror $18_3$ and is irradiated on the DUT 5. The resulting photon echo FID signal 9 from the DUT 41 is guided by the mirror $18_4$ to be supplied to the beam splitter $17_2$ where it is mixed with the reference light beam 7. As noted above with reference to FIG. 2A, since the reference light beam 7 is frequency shifted by the frequency shifter 16, the mixed signal 10 is a light signal having the beat frequency of which is a difference between the reference light beam 7 and the photon echo FID signal 9.

In the same manner as described with reference to FIG. 2A, the mixed signal 10 is received by the birefringence prism 21 whereby polarization components are separated one another. The photon echo FID signal in each polarization component is converted to the electric signal which is further transformed to a Fourier spectra.

In the example of FIG. 2, the birefringence prism is a Wollaston prism which can separate the polarization components in the incoming light signal. Other type of prism can also be applicable so long as it is able to deviates the polarized plane of an incoming light signal. As is known in the art, such a prism includes a Rochon prism, a Nicol prism or a Glan-Thompson prism.

In the foregoing examples in FIGS. 1 and 2, the light pulse train may be applied to the device under test just once to obtain the information necessary for analyzing the hole burning effect. However, preferably, the light pulse train may be repeatedly applied to the device under test so that the data are added and averaged by the measurement system of the present invention. As is well known in the art, such averaging results in an increased sensitivity because of an improvement of S/N ratio. Such averaging is carried out for the output of the A/D converter or for the results of the Fourier transformation.

As has been described in the foregoing, according to the present invention, the hole burning effect measurement system can measure photochemical hole burning effects related to both an optical communication field and an optical memory field by the same technical concept, i.e. the photon echo and heterodyne technology. The hole burning effect measurement system of the present invention is capable of analyzing the photochemical hole burning effects in the optical memory as well as in the optical communication devices such as an optical amplifier or an optical fiber.

The hole burning effect measurement system of the present invention accurately analyzes the photochemical hole burning effect with the use of low power light pulses so that the hole burning effect is not affected by the temperature of the host materials. Further, the hole burning effect measurement system analyzes the photochemical hole burning effect with high sensitivity by utilizing an averaging technology in processing photon echoes from the optical device under test induced by the measurement system.

What is claimed is:

1. A hole burning measurement system for analyzing a photochemical hole burning effect in an optical device under, comprising:

a light source for generating a coherent light beam;

a first beam splitter for splitting said coherent light beam into two light beams;

an optical frequency shifter for shifting a frequency of one of said two light beams splitted by said first beam splitter to form a reference light beam;

an optical switch for switching the other light beam splitted by said first beam splitter to form a pulse train in a form predetermined for inducing photon echoes in said optical device under test;

a circular polarization converter for circularly polarizing said pulse train from said optical switch to form a circularly polarized light pulse train to be applied to said optical device under test;

a second beam splitter for mixing said reference light beam and a free induction decay (FID) signal of said photon echo induced by said pulse train in said optical device under test;

a photo detector for receiving a mixed signal from said second beam splitter and converting the same to a corresponding electric signal;

an analog-to-digital converter for converting said electric signal to corresponding digital data; and a Fourier transformer for converting said digital data from said analog-to-digital converter to frequency domain data showing said hole burning effect in a form of frequency spectrum.

2. A hole burning measurement system as defined in claim 1, wherein said optical device under test is a transmission type device through which said pulse train is transmitted thereby said FID signal of said photon echo is generated from said optical device under test.

3. A hole burning measurement system as defined in claim 1, wherein said optical device under test is a reflection type device, said hole burning measurement system further includes a reflecting plate for guiding said pulse train to said optical device under test and another reflecting plate for guiding said FID signal of said photon echo generated by said optical device under test to said second beam splitter.

4. A hole burning measurement system as defined in claim 1, wherein said digital data are obtained in a plurality of times and averaged whereby a signal to noise ratio increases.

5. A hole burning measurement system as defined in claim 1, further includes a lens positioned between said second beam splitter and said photo detector to focus a light beam combined by said second beam splitter.

6. A hole burning measurement system as defined in claim 1, wherein said circular polarization converter includes a polarizer and a ¼ wavelength plate.

7. A hole burning measurement system as defined in claim 1, wherein said photo detector is formed of a photo diode which converts an incoming optical signal to a corresponding electric signal.

8. A hole burning measurement system for analyzing a photochemical hole burning effect in an optical device under, comprising:

a light source for generating a coherent light beam;

a first beam splitter for splitting said coherent light beam into two light beams;

an optical frequency shifter for shifting a frequency of one of said two light beams splitted by said first beam splitter to form a reference light beam;

an optical switch for switching the other light beam splitted by said first beam splitter to form a pulse train in a form predetermined for inducing photon echoes in said optical device under test;

a circular polarization converter for circularly polarizing said pulse train from said optical switch to form a circularly polarized light pulse train to be applied to said optical device under test;

a second beam splitter for mixing said reference light beam and a free induction decay (FID) signal of said photon echo induced by said pulse train in said optical device under test;

a birefringent prism for separating polarization components, which are perpendicular with each other, in said FID signal of said photon echo in a mixed signal from said second beam splitter;

a pair of photo detectors each of which receiving one of said polarization components from said birefringent prism and converting the same to a corresponding electric signal;

a pair of analog-to-digital converters for converting one of said electric signals to corresponding digital data; and a Fourier transformer for converting said digital data from said pair of analog-to-digital converters to frequency domain data showing polarization hole burning effects in said optical device under test in a form of frequency spectrum.

9. A hole burning measurement system as defined in claim 8, wherein said birefringence prism is a type of prism including a Wollaston prism, a Rochon prism, a Nicol prism or a Glan-Thompson prism which is able to deviates polarized plane of an incoming light signal.

10. A hole burning measurement system as defined in claim 8, wherein said optical device under test is a transmission type device through which said pulse train is transmitted thereby said FID signal of said photon echo is generated from said optical device under test.

11. A hole burning measurement system as defined in claim 8, wherein said optical device under test is a reflection type device, said hole burning measurement system further includes a reflecting plate for guiding said pulse train to said optical device under test and another reflecting plate for guiding said FID signal of said photon echo generated by said optical device under test to said second beam splitter.

12. A hole burning measurement system as defined in claim 8, wherein said digital data are obtained in a plurality of times and averaged whereby a signal to noise ratio increases.

13. A hole burning measurement system as defined in claim 8, further includes a lens positioned between said second beam splitter and said photo detector to focus a light beam combined by said second beam splitter.

14. A hole burning measurement system as defined in claim 8, wherein said circular polarization converter includes a polarizer and a ¼ wavelength plate.

15. A hole burning measurement system as defined in claim 8, wherein said photo detector is formed of a photo diode which converts an incoming optical signal to a corresponding electric signal.

* * * * *